United States Patent [19]

Johnson et al.

[11] Patent Number: 4,909,317

[45] Date of Patent: Mar. 20, 1990

[54] CONDENSER, HERMETIC SEALING, HIGH AND LOW TEMPERATURE RESISTANT

[75] Inventors: Sean A. Johnson; Nancy K. Roberts, both of Chino; Richard P. Lutz, Jr., Diamond Bar, all of Calif.

[73] Assignee: General Dynamics Corp., Pomona Div., Pomona, Calif.

[21] Appl. No.: 201,819

[22] Filed: Jun. 3, 1988

[51] Int. Cl.$^4$ .............................................. F28B 1/00
[52] U.S. Cl. ................................................... 165/110
[58] Field of Search ...................................... 165/110

[56] References Cited

U.S. PATENT DOCUMENTS

| | | | |
|---|---|---|---|
| 1,798,032 | 3/1931 | Rice . | |
| 1,813,667 | 7/1931 | Hartenstein | 165/110 |
| 1,998,679 | 4/1935 | Linde | 165/110 |
| 2,375,069 | 5/1945 | Bennett et al. | 165/110 |
| 2,659,452 | 11/1953 | Gaydasch | 165/110 |
| 2,687,185 | 8/1954 | McChesney | 183/32 |
| 2,980,172 | 4/1961 | Thompson | 165/110 |
| 3,487,692 | 1/1970 | Cook, Jr. | 73/421 |
| 3,824,167 | 7/1974 | Oswin et al. | 204/195 R |
| 3,956,921 | 5/1976 | Himes et al. | 73/421.5 R |
| 3,985,624 | 10/1976 | Prevest et al. | 196/132 |
| 4,137,773 | 2/1979 | Loncaric | 73/421 B |
| 4,335,620 | 6/1982 | Adams | 73/863.11 |
| 4,626,387 | 12/1986 | Dodds | 165/110 |

*Primary Examiner*—Henry A. Bennet
*Assistant Examiner*—Denise L. Ferensic
*Attorney, Agent, or Firm*—Henry Bissell; Leo R. Carroll

[57] ABSTRACT

A condensing apparatus is provided which can be used in gas chromatography measurements to determine N-methyl-2-pyrrolidone (NMP) content in polyimide prepreg. The condenser comprises a straight vertical section of thin-walled copper tubing followed by an ascending helical coil surrounding the straight section. The condenser is equipped with valves at the inlet and outlet which are capable of withstanding the combination of high and low temperatures as well as being resistant to damage by aggressive solvents. Liquid condensate accumulates at the bottom of the coil, making decanting easy. The condenser apparatus of the present invention yields very high collection efficiencies for volatile mixtures with a very wide range of boiling points. The condenser is very compact and lightweight and does not require any packing insulation to achieve the high collection efficiencies. Maintenance and cleaning are greatly simplified by the absence of packing. The all-metal construction of the condenser makes it extremely rugged and assures an operating life of hundreds of cycles.

8 Claims, 1 Drawing Sheet

CONDENSER, HERMETIC SEALING, HIGH AND LOW TEMPERATURE RESISTANT

This invention was made with Government support under Contract No. N00024-85-C-5501 awarded by the U.S. Navy. The Government has certain rights in this invention.

RELATED APPLICATIONS

This application is related to two other applications which are being filed concurrently herewith, Ser. No. 07/201,985 entitled: "Sample Containment Chamber, Corrosion Resistant Steel, Gas Tight," by Sean A. Johnson et al, and Ser. No. 07/201,820 entitled: "Method and Apparatus for the Determination of N-Methyl-2-Pyrrolidone (NMP) Content in Polyimide Resin Pre-Impregnated Fabric," by Sean A. Johnson et al, both assigned to the assignee of the present application. The inventions of those applications are subject to the same rights clause set forth above.

BACKGROUND OF THE INVENTION

1. Field of the Invention

This invention relates to condenser apparatus for collecting a mixture of high- and low-boiling point components and, more particularly, to a condenser with extremely high collection efficiency which can be hermetically sealed under either high or low temperatures.

2. Description of the Related Art

Methods of quantitative analysis such as gas chromatography can be used to measure the amounts of volatile components in a sample of material. The sample is heated in a containment chamber and the evolved volatile products are condensed and collected for subsequent analysis. Often the volatile products that are condensed have a very wide range of boiling points, so that the condenser apparatus used must be capable of operation over a very wide range of temperatures. High temperatures are required in the transport line between the containment chamber and the inlet to the condenser to prevent condensation of the high-boiling-point components in the line. Extremely high collection efficiencies are required for accurate analysis, so that the condenser is required to have a large amount of interior surface area in relation to the amounts of volatiles being collected. Because of the volatility of the components being collected, the condenser must be capable of being hermetically sealed after the completion of the collection phase of the procedure. The components employed for hermetic sealing must be capable of withstanding a combination of high and low temperatures as well as resisting damage by aggressive solvents.

Such a condenser apparatus as has been described above is necessary for the successful determination of the NMP content in prepreg by gas chromatography measurements. A satisfactory condenser would be able to operate at extremely high collection efficiencies with solvent mixtures (vapor, fluid, and solids) of widely different volatilities and high solvent powers. Various areas of the condenser would have to operate at temperatures ranging from greater than 500° F. down to cryogenic temperatures. It would be a great advantage if the condenser apparatus were easy to assemble and disassemble and to operate trouble-free even with condensed solid phases present. It would be additionally advantageous if the decanting of liquid condensates for subsequent analysis and the cleaning of the condenser in preparation for re-use were extremely easy procedures. Other desirable features would include the capability of quantitating sub-milligram amounts of condensed material quickly and with a high degree of accuracy. Finally, the use of materials that render the condenser very easy and inexpensive to construct, and that assure an operating life of many hundreds of cycles, would be another valuable feature. Some representative examples of the related art are briefly described and discussed below.

U.S. Pat. No. 1,798,032 to Rice describes a method and apparatus for removing superheat from steam, testing for suspended material, and condensing the steam for analysis.

U.S. Pat. No. 2,687,185 to McChesney describes a method and apparatus for obtaining condensate from vapor while avoiding contamination by gases present in the vapor.

U.S. Pat. No. 3,487,692 to Cook, Jr. describes a method and apparatus for sampling refrigerated mixtures of volatile liquids without fractionation of the samples. The apparatus described is not a condenser, but is designed to heat samples at constant volume with varying temperatures and pressures without affecting any phase change. The apparatus is not designed to operate under dynamic flow conditions.

U.S. Pat. No. 3,824,167 to Oswin et al describes an apparatus for detection and quantitative measurement of a select gas in a gaseous medium, such as alcohol in the breath or carbon monoxide in the atmosphere. The device comprises intake and flow control means for the gas sample, and an electrochemical cell for detection.

U.S. Pat. No. 3,956,921 to Himes et al describes an apparatus consisting of a simple tubular condensing coil fitted with a throttling valve and connected to a reservoir and vacuum chamber. The apparatus can be used for sampling fluid materials over a given period of time from a moving fluid stream such as a flue gas from a chimney or stack.

U.S. Pat. No. 3,985,624 to Prevost et al describes a method and apparatus for continuous sampling of vaporized fractions of crude petroleum, especially in crude petroleum topping columns.

U.S. Pat. No. 4,137,773 Loncaric describes a method and apparatus for obtaining liquid samples from petroleum handling equipment without the danger of electrostatic discharge.

U.S Pat. No. 4,335,620 to Adams describes a temperature controlled sample carrier apparatus usable in liquid chromatography. The apparatus contains a heat transfer coil which is not used to effect any phase change of interior or exterior fluids.

None of the examples of related art described above provides a condenser which can be routinely connected and disconnected from a main apparatus, which can operate trouble-free even with condensed solid phases present, which allows the quantitative determination of sub-milligram amounts of condensed material quickly and with a high degree of accuracy, which is capable of gas tight operation at extremely high collection efficiencies with solvent mixtures of widely different volatilities and high solvent power, and from which easy decanting of liquid condensate for subsequent analysis is possible, with a simple procedure for cleaning in preparation for re-use.

SUMMARY OF THE INvENTION

A condensing apparatus is provided in accordance with the present invention which can be used in gas chromatography measurements to determine N-methyl-2-pyrrolidone (NMP) content in polyimide prepreg. To achieve an extremely high collection efficiency the condensing apparatus has a large amount of interior surface area in relation to the amounts of volatiles being collected. The condenser is capable of being hermetically sealed after completion of the collection phase of the NMP content determination procedure. The condenser comprises a straight vertical section of thin-walled copper tubing followed by an ascending helical coil surrounding the straight section. The condenser is equipped with valves at the inlet and outlet which are capable of withstanding a combination of high and low temperatures as well as being resistant to damage by aggressive solvents. Liquid condensate accumulates at the bottom of the coil, making decanting extremely easy.

The condenser apparatus of the present invention yields very high collection efficiencies for mixtures with a very wide range of boiling points. The condenser is very compact and lightweight (approximately one pound) and does not require any packing or insulation to achieve the high collection efficiencies. Maintenance and cleaning of the condenser and the decanting of condensate for analysis are greatly simplified by the absence of packing.

The large internal surface area and the flow path render the condenser resistant to blockage by frozen condensate. Additionally, the inlet section and coil pattern cause the liquid condensate to accumulate at the bottom. Decanting of the liquid condensate is very simple, since nearly complete expulsion of the condenser contents is accomplished by inverting the condenser over a collection vessel and opening the inlet valve.

The condenser is constructed from easy-to-obtain, inexpensive, off-the-shelf items. Manufacture of the condenser does not require machining, drawing, or glass blowing. The all-metal construction of the condenser makes it extremely rugged and assures an operating life of hundreds of cycles.

BRIEF DESCRIPTION OF THE DRAWING

A better understanding of the present invention may be realized from a consideration of the following detailed description, taken in conjunction with the accompanying drawing in which.

DESCRIPTION OF THE PREFERRED EMBODIMENT

As described in the application Ser. No. 07/20/820 "Method and Apparatus for the Determination of N-Methyl-2-Pyrrolidone (NMP) Content in Polyimide Resin Pre-Impregnated Fabric," assigned to the assignee of the present application, the description of which is incorporated herein by reference, the NMP content test measures amounts of reactive and nonreactive volatiles in polyimide prepreg samples. The samples are heated in a containment chamber and the volatile products evolved are condensed and collected for subsequent analysis. The volatile products that are condensed have a very wide range of boiling points, from 78° C. (173° F.) to 202° C. (396° F.). The transport line between the containment chamber and the inlet to the condensing apparatus must be maintained at high temperatures to prevent condensation of the high boiling point component NMP in the line.

Figure 1:
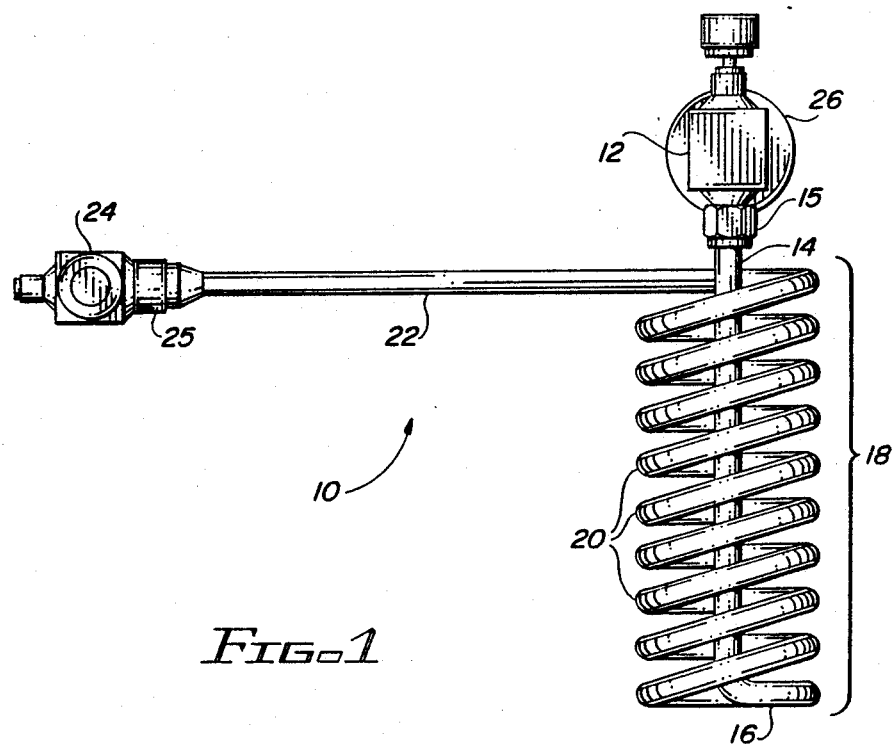
FIG. 1 is a side elevational view of a condenser apparatus in accordance with the present invention.
Figure 2:
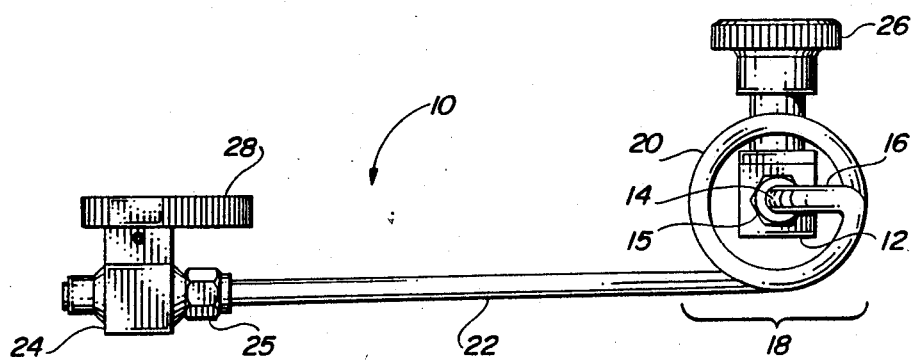
FIG. 2 is a bottom plan view of the condenser apparatus shown in FIG. 1.

In accordance with the present invention a hermetic sealing, high- and low-temperature resistant condenser is provided which serves as an integral component in the determination of NMP content in polyimide prepreg by gas chromatography. FIG. 1 is a side elevational view of a condenser 10 in accordance with the present invention. Condenser 10 is constructed from thin-walled copper tubing with a nominal outside diameter of ¼ inch. An inlet valve 12 is a corrosion resistant steel bellows-type valve. A valve manufactured by Nupro Corp., Arcadia, California, designated as SS-4H, is suitable for use as inlet valve 12. Valve 12 is attached to an inlet section 14 via an inlet coupling 15. Inlet section 14 of condenser 10 consists of a straight vertical portion 6 +/−1 inches long. At the bottom of the vertical drop of inlet section 14, the tubing undergoes a roughly right-angled bend through a short section 16 before being formed into an ascending coil 18 which is 2.0 +/−0.5 inches in diameter with a total of ten circular turns 20. An outlet segment 22 is 6 +/−1 inches long and extends roughly at right angles to vertical inlet segment 14 from an uppermost turn of coil 18. An outlet valve 24 connected by outlet coupling 25 to the end of outlet segment 22 is a quarter turn, brass-plug type valve with fluoroplastic-coated fluoroelastomer seals. A suitable valve for outlet valve 24 is manufactured by Nupro Corp., Arcadia, California and designated as B-4P4T. FIG. 2 shows additional details in a bottom plan view of condenser 10. Inlet valve handle 26 and outlet valve handle 28 can be seen.

Condenser 10 employs a stainless steel bellows-type valve for inlet valve 12 because of the high temperatures of the volatiles at the inlet, up to 550° F. Stainless steel is also resistant to the high solvent power of the volatile components. Inlet valve 12 must operate in such a manner that no contaminants are introduced into the volatile stream. Unwanted contaminants would include lubricants, greases, and decomposing seal materials, for example.

The straight vertical drop of inlet section 14 of condenser 10 after inlet valve 12 causes the heated volatile products to travel well past the condenser inlet. Condensation and freezing of the volatile products is distributed over a large fraction of the length of the coil 18.

The turns 20 of the coil 18 of condenser 10 are arranged in an ascending spiral so that any condensate frozen in the turns 20 will accumulate at the bottom of the condenser after thawing when the test procedure is concluded.

Outlet valve 24 provides the second seal to assure complete retention of condensed volatiles. The seal components of outlet valve 24 are fluoroelastomers and fluoroplastics which are impervious to the volatile components and cleaning solvents used at the temperatures experienced by the outlet valve 24.

Copper tubing is used for the main body of condenser 10 because it provides excellent heat transfer, is easily formed to the dimensions required, and is extremely rugged and durable under industrial handling conditions. The condenser 10 described above yields very high collection efficiencies (defined as the amount of volatiles collected divided by the amount of volatiles generated) for mixtures with a very wide range of boiling points, yet condenser 10 is very compact and lightweight (approximately one pound). Condenser 10 of the present invention does not require any packing or insulation to achieve high collection efficiencies. Maintenance and cleaning of condenser 10 is greatly simplified by the absence of packing, as is the decanting of condensate for subsequent analysis.

The large internal surface area and the flow path render condenser 10 resistant to blockage by frozen condensate. Additionally, the shape of inlet section 14 and coil 18 causes the liquid condensate to accumulate at the bottom. This makes decanting of the liquid condensate extremely easy, since nearly total expulsion of the condenser contents can be accomplished simply by inverting condenser 10 over a collection vessel and opening inlet valve 12.

Condenser 10 is constructed from easy-to-obtain, inexpensive, off-the-shelf items. It can be manufactured quickly and in a simple manner that obviates the need for machining, drawing, or glass blowing. An operating life of hundreds of cycles is assured by the all-metal construction of condenser 10.

Condenser 10 is constructed in such a way that the inlet valve 12 and an adjacent portion of inlet section 14 can be operated at very high temperatures while the body consisting of the rest of straight-line section 14 and coil 18 can be operated at extremely low temperatures. The provision of inlet valve 12 and outlet valve 24 assures hermetic sealing of condenser 10 after collection of volatiles is complete. This permits an accuracy of collection and test results for this volatile component system that are an order of magnitude greater than would be possible without the valves 12 and 24. The ruggedness, simplicity, and low cost of the condenser 10 in combination with the high collection efficiencies achieved is unique. Other attempts to accomplish similar results require costly manufacturing techniques and produce a condenser that is typically cumbersome and extremely fragile.

The condenser 10 described above in accordance with the present invention would also be useful for collection, analysis, and quantitation of a wide range of other volatilized systems, including chemical systems which contain components that are gaseous at standard temperature and pressure. Condenser 10 is also inherently capable of operating with inlet gas stream temperatures up to 1200° F. and condenser body cooling medium temperatures down to at least those of liquid nitrogen ($-320°$ F.).

The condenser 10 of the present invention described above will find commercial application wherever it is required to separate, accurately quantitate, and recover the volatile components from a mixture of volatile and nonvolatile species. Use of this invention could displace many of the liquid-liquid and liquid-solid extraction procedures currently practiced.

Although there have been described above specific arrangements of a hermetic-sealing, high- and low-temperature resistant condenser in accordance with the invention for the purpose of illustrating the manner in which the invention may be used to advantage, it will be appreciated that the invention is not limited thereto. Accordingly, any and all modifications, variations, or equivalent arrangements which may occur to those skilled in the art should be considered to be within the scope of the invention as defined in the annexed claims.

What is claimed is:

1. A hermetic sealing, high- and low-temperature resistant condensing apparatus for collection of solvent mixtures of widely different volatilities and high solvent power with high collection efficiency comprising:
    a condenser body having a gastight flow path therethrough with an inlet end and an outlet end, said condenser body being in the form of a continuous metal tube which is devoid of interruption or external connection between said inlet and outlet ends;
    inlet valve means on said inlet end of said condenser body for controlling a gas flow into said body; and
    outlet valve means on said outlet end of said condenser body for controlling a gas flow out of said body;
    said condenser body comprising:
        a substantially straight-line segment of metallic tubing extending directly from said inlet end, having a distal portion remote from said inlet end for collecting liquid condensate therein;
        a coil portion surrounding said straight-line segment;
        said straight-line segment and said coil portion being integrally formed with said distal portion being continued as a first end turn of said coil portion; and
        an outlet segment between a second end turn of said coil portion and said outlet end extending from said coil portion substantially perpendicular to said straight-line segment.

2. The condensing apparatus of claim 1 wherein said coil portion comprises a plurality of ascending turns from said distal portion to said outlet segment and said apparatus is devoid of insulated packing material.

3. The condensing apparatus of claim 2 wherein said straight-line segment, said coil portion, and said outlet segment are formed with thin-walled copper tubing.

4. The condensing apparatus of claim 3 wherein said straight-line segment is approximately 5 to 7 inches long, said coil portion has a diameter of approximately 1.5 to 2.5 inches, and said outlet segment is approximately 5 to 7 inches long.

5. The condensing apparatus of claim 2 wherein said coil portion comprises between 7 and 13 turns.

6. The condensing apparatus of claim 1 wherein said inlet valve is a corrosion resistant steel bellows-type valve.

7. The condensing apparatus of claim 1 wherein said outlet valve is a quarter-turn brass-plug type valve with fluoroplastic-coated fluoroelastomer seals.

8. The condensing apparatus of claim 1 further comprising:
    inlet coupling means for coupling said inlet valve means to said inlet end; and
    outlet coupling means for coupling said outlet valve means to said outlet end.

* * * * *